(12) United States Patent
Deslauriers et al.

(10) Patent No.: US 7,041,056 B2
(45) Date of Patent: May 9, 2006

(54) INFLATABLE SPECULUMS

(76) Inventors: Richard J. Deslauriers, 87 Carmel Hill Rd., Woodbury, CT (US) 06798; Robert T. Potash, 23 Glen Cir., Seymour, CT (US) 06483; Lewis W. Chappel, 71 Burwell Rd., New Hartford, CT (US) 06057

( * ) Notice: Subject to any disclaimer, the term of this patent is extended or adjusted under 35 U.S.C. 154(b) by 0 days.

(21) Appl. No.: 10/458,202

(22) Filed: Jun. 11, 2003

(65) Prior Publication Data

US 2003/0199737 A1    Oct. 23, 2003

Related U.S. Application Data

(63) Continuation-in-part of application No. 09/972,254, filed on Oct. 9, 2001, now abandoned, and a continuation-in-part of application No. 10/259,675, filed on Sep. 30, 2002, now abandoned.

(51) Int. Cl.
*A61B 1/32* (2006.01)
(52) U.S. Cl. .................................................. 600/208
(58) Field of Classification Search ................ 600/207, 600/208, 223, 206; 606/193
See application file for complete search history.

(56) References Cited

U.S. PATENT DOCUMENTS

| 2,548,602 | A | * | 4/1951 | Greenburg | .................. | 600/207 |
| 3,774,596 | A | | 11/1973 | Cook | | |
| 3,831,587 | A | | 8/1974 | Boyd | | |
| 5,179,938 | A | | 1/1993 | Lonky | | |
| 5,329,938 | A | | 7/1994 | Lonky | | |
| 5,342,385 | A | | 8/1994 | Norelli et al. | .............. | 606/193 |
| 2002/0013601 | A1 | | 1/2002 | Nobles et al. | .............. | 606/193 |

FOREIGN PATENT DOCUMENTS

| WO | WO9307800 | 4/1993 |
| WO | WO9724975 | 7/1997 |

* cited by examiner

*Primary Examiner*—Cary E. O'Connor
(74) *Attorney, Agent, or Firm*—Baker Botts L.L.P.

(57) ABSTRACT

An inflatable speculum adapted to be positioned within an orifice includes an inflatable bladder. In an embodiment, when the inflatable bladder is inflated, the inflatable bladder includes a baffle member. The baffle member includes a plurality of baffles, and each of the plurality of baffles has a substantially trapezoidal cross-sectional shape. The inflatable bladder also includes an opening formed between a first end of the inflatable bladder and a second end of the inflatable bladder for viewing an inside of the orifice. In another embodiment, when the inflatable bladder is inflated, the inflatable bladder includes the opening formed between the first end of the inflatable bladder and the second end of the inflatable bladder, a pump and inflation line for inflating the inflatable bladder, and an applicator. Specifically, when the inflatable bladder is not inflated, a first member of the applicator encloses the inflatable bladder and a second member of the applicator is attached to the inflation line, and when the inflatable bladder is inflated, a portion of the first member is torn and the second member remains attached to the inflation line.

33 Claims, 8 Drawing Sheets

INFLATABLE SPECULUMS

The present application claims from priority from and is a continuation in part of U.S. patent application Ser. No. 09/972,254, entitled "Dilating Inflatable Speculum," and filed on Oct. 9, 2001 now abandoned, and U.S. patent application Ser. No. 10/259,675, filed on Sep. 30, 2002 now abandoned, the disclosures of which are incorporated herein by reference in their entirety.

BACKGROUND OF THE INVENTION

1. Field of the Invention

The present invention relates generally to speculums. In particular, the present invention is directed toward speculums adapted to positioned inside an orifice, such as a vagina, and inflated for viewing an inside of the orifice.

2. Description of Related Art

Referring to FIGS. 1a and 1b, a known speculum 100, such as the speculum described in U.S. Pat. No. 5,342,385, the disclosure of which is incorporated herein by reference in its entirety, includes an inflatable bladder 10. Inflatable bladder 10 includes a first flexible layer 20, a second flexible layer 30, and a plurality of baffles 40. Speculum 100 also includes an inflation line 50 attached to inflatable bladder 10, and a pump 60 attached to inflation line. Moreover, speculum 100 includes an applicator 70. Specifically, applicator 70 includes a plunger 70a for positioning speculum 100 within the orifice, and a removable, insertion tube 70b. In operation, speculum 100 is inserted inside an orifice (not shown) using applicator 70, and insertion tube 70b is removed from inside the orifice. Inflatable bladder 10 subsequently is inflated via pump 60 and inflation line 50. Inflating inflatable bladder 10 creates an opening 80 between a first end and a second end of inflatable bladder 10 for viewing an inside of the orifice. Moreover, first flexible layer 20, second flexible layer 30, and baffles 40 inflate, such that baffles 40 have a triangle-shaped cross-sectional area.

Nevertheless, because baffles 40 have a triangle-shaped cross-sectional area, if the walls of the orifice apply a predetermined amount of pressure to inflatable bladder 10, baffles 40 collapse. Further, it is necessary to remove insertion tube 70b from inside the orifice before inflating inflatable bladder 10. Moreover, if a user of speculum 100 wishes to obtain a sample from inside the orifice, the user removes speculum 100 before obtaining such sample.

SUMMARY OF THE INVENTION

Therefore, a need has arisen for inflatable speculums which overcome these and other shortcomings of the related art. A technical advantage of the present invention is that the baffles may have a trapezoidal cross-sectional shape. Consequently, when the orifice applies the predetermined amount of pressure to the inflatable bladder, the baffles do not collapse. Further, the applicator may be a plastic sheath, e.g., a perforated plastic sheath, which encloses the inflatable bladder and is attached to the inflation line, such that when the inflatable bladder is inflated, the applicator readily tears. Because the applicator remains attached to the inflation line, the applicator is removed from the orifice when the speculum is removed from the orifice. Moreover, an opening may be formed through a wall of the inflatable bladder, such that the user of the speculum may obtain a sample from inside the orifice via the opening in the wall without having to first remove the speculum.

According to an embodiment of the present invention, an inflatable speculum adapted to be positioned within an orifice comprises an inflatable bladder. When the inflatable bladder is inflated, the inflatable bladder comprises a baffle member, and the baffle member comprises a plurality of baffles. Specifically, each of the plurality of baffles has a substantially trapezoidal cross-sectional shape. The inflatable baffle also comprises an opening formed between a first end of the inflatable bladder and a second end of the inflatable bladder for viewing an inside of the orifice.

According to another embodiment of the present invention, an inflatable speculum adapted to be positioned within an orifice comprises an inflatable bladder. When the inflatable bladder is inflated, the inflatable bladder comprises a first opening formed between a first end of the inflatable bladder and a second end of the inflatable bladder for viewing an inside of the orifice. The inflatable bladder also comprises at least one second opening formed through a wall of the inflatable bladder for allowing access to at least one wall of the orifice, e.g., for obtaining a sample from the wall of the orifice.

According to yet another embodiment of the present invention, an inflatable speculum adapted to be positioned within an orifice comprises an inflatable bladder. When the inflatable bladder is inflated, the inflatable bladder comprises an opening formed between a first end of the inflatable bladder and a second end of the inflatable bladder. The speculum also comprises means for inflating the inflatable bladder, e.g., a pump and an inflation line, and an applicator. Specifically, when the inflatable bladder is not inflated, a first member of the applicator encloses the inflatable bladder, and a second member of the applicator is attached to the means for inflating. Moreover, when the inflatable bladder is inflated, a particular portion of the first member is torn and the second member remains attached to the means for inflating.

Other objects, features, and advantages will be apparent to persons of ordinary skill in the art in view of the following detailed description of the invention and the accompanying drawings.

BRIEF DESCRIPTION OF THE DRAWINGS

For a more complete understanding of the present invention, needs satisfied thereby, and objects, features, and advantages thereof, reference now is made to the following descriptions taken in connection with the accompanying drawings.

DETAILED DESCRIPTION OF PREFERRED EMBODIMENTS

Figure 1A:
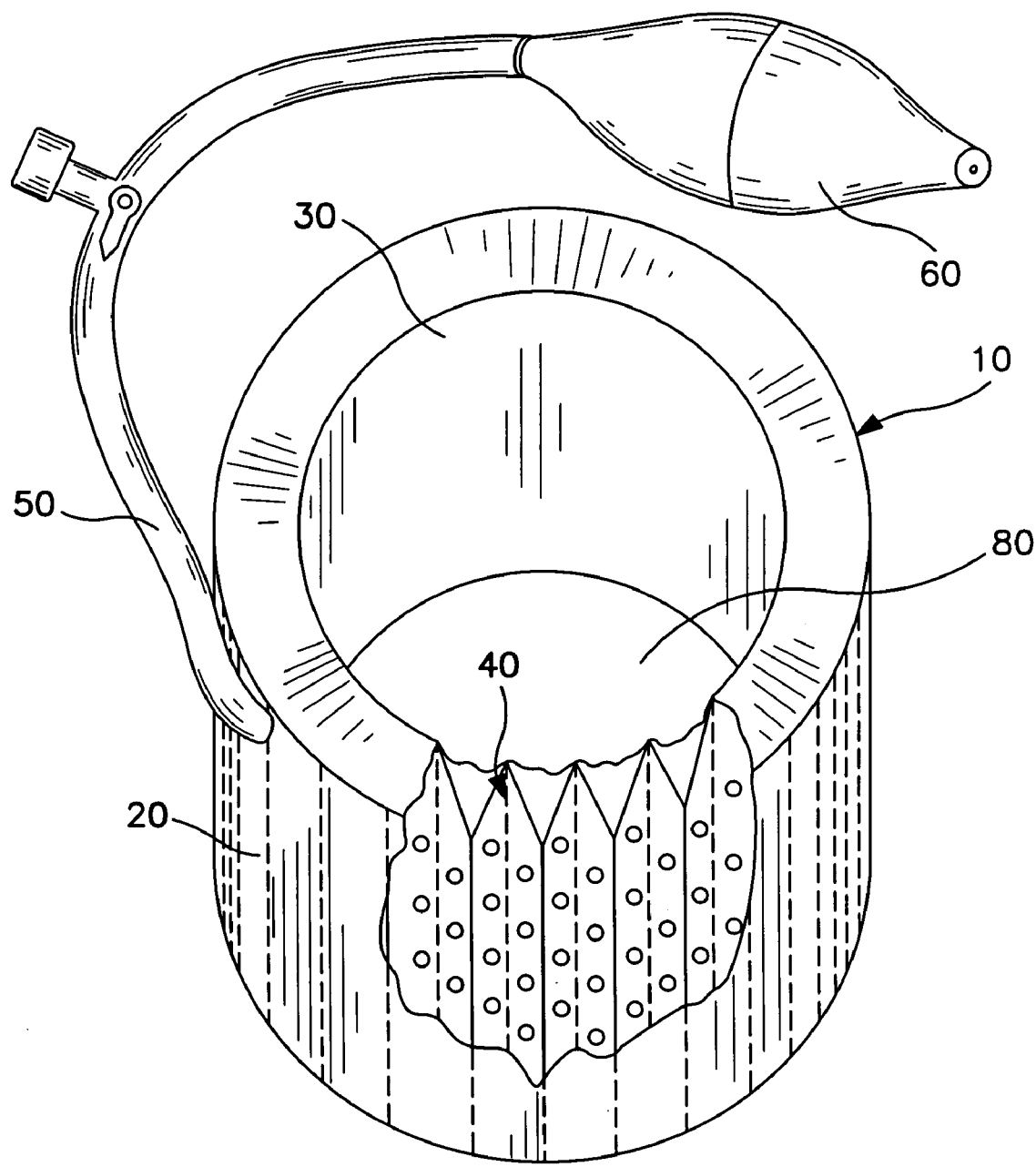
FIGS. 1a and 1b are a cross-section view and perspective view, respectively, of a known speculum.
Figure 1B:
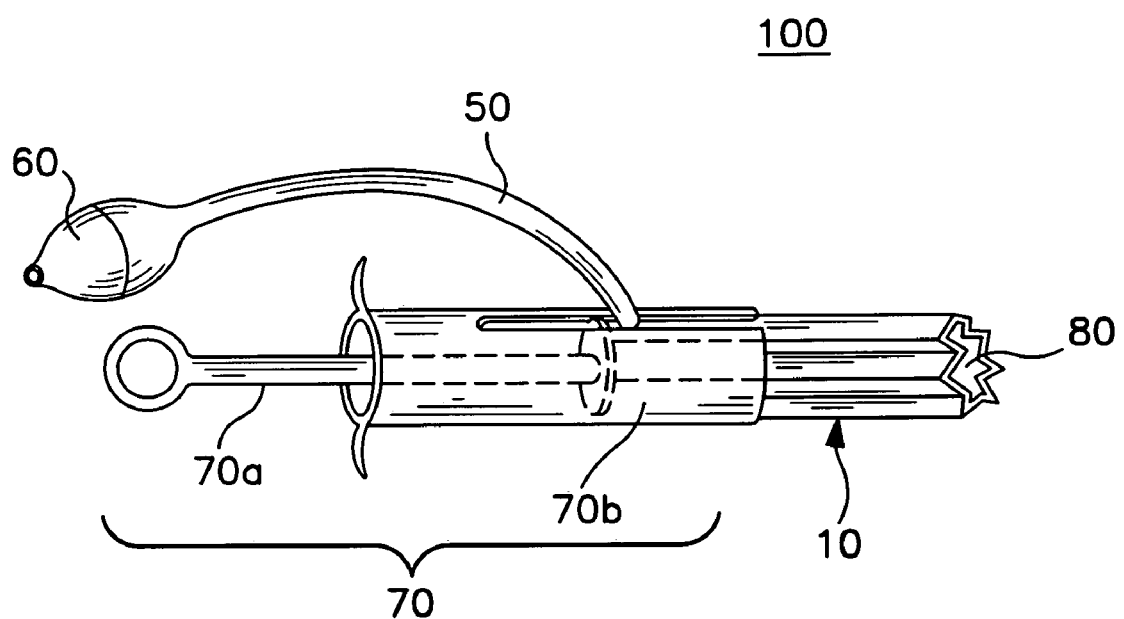
Figure 2:
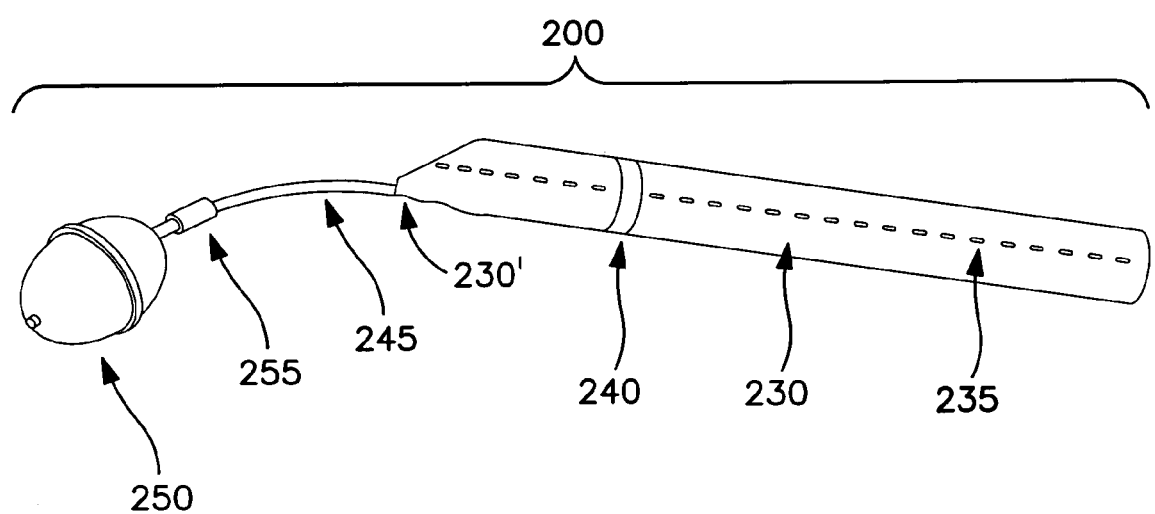
FIG. 2 is a perspective view of a speculum depicting a portion of an applicator attached to an inflation line, according to an embodiment of the present invention.
Figure 3:
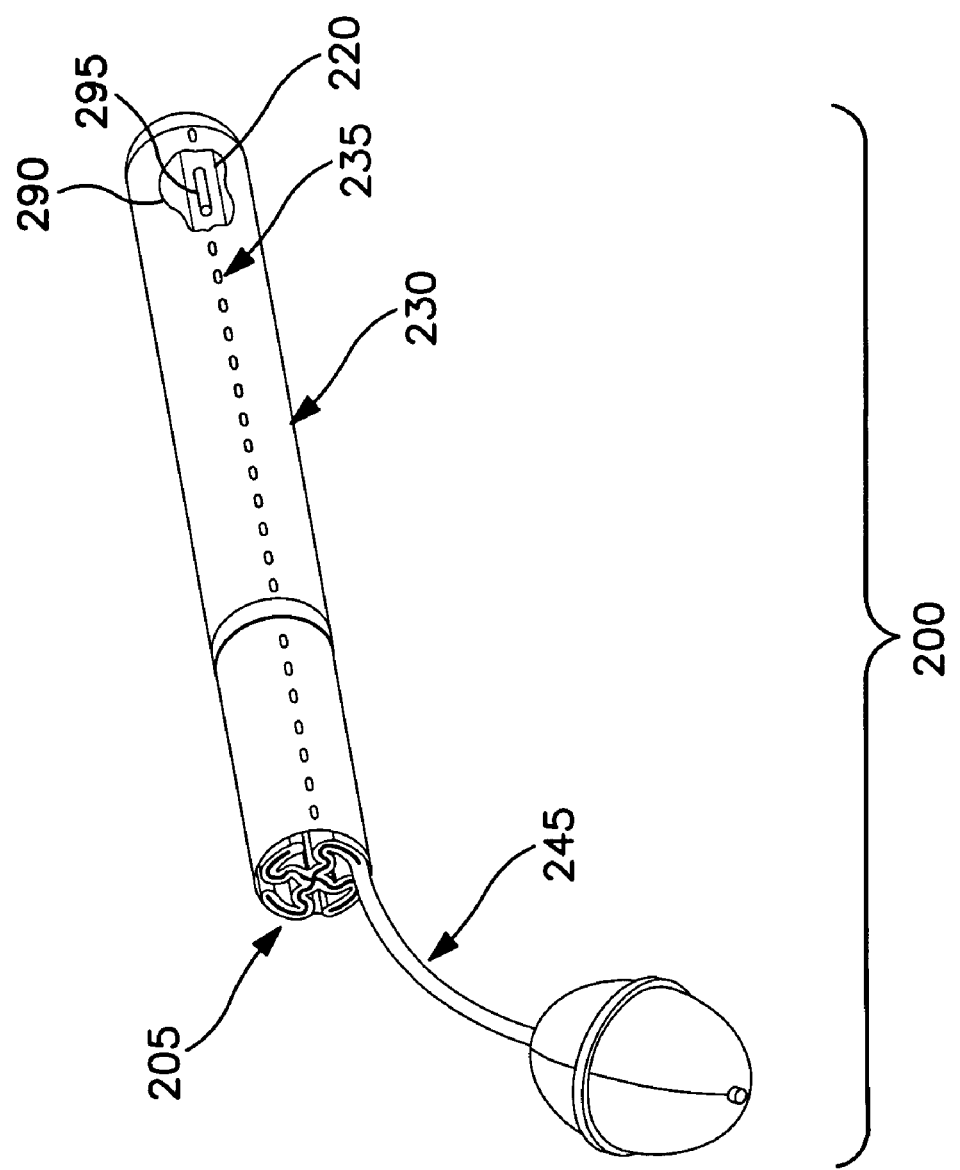
FIG. 3 is a perspective view of the speculum of FIG. 2, with the portion of the applicator attached to the inflation line removed to depict a cross-sectional view of a bladder of the speculum and with a portion of the applicator's sheath cut away to depict a light source positioned within one of the baffles, according to an embodiment of the present invention.
Figure 4:
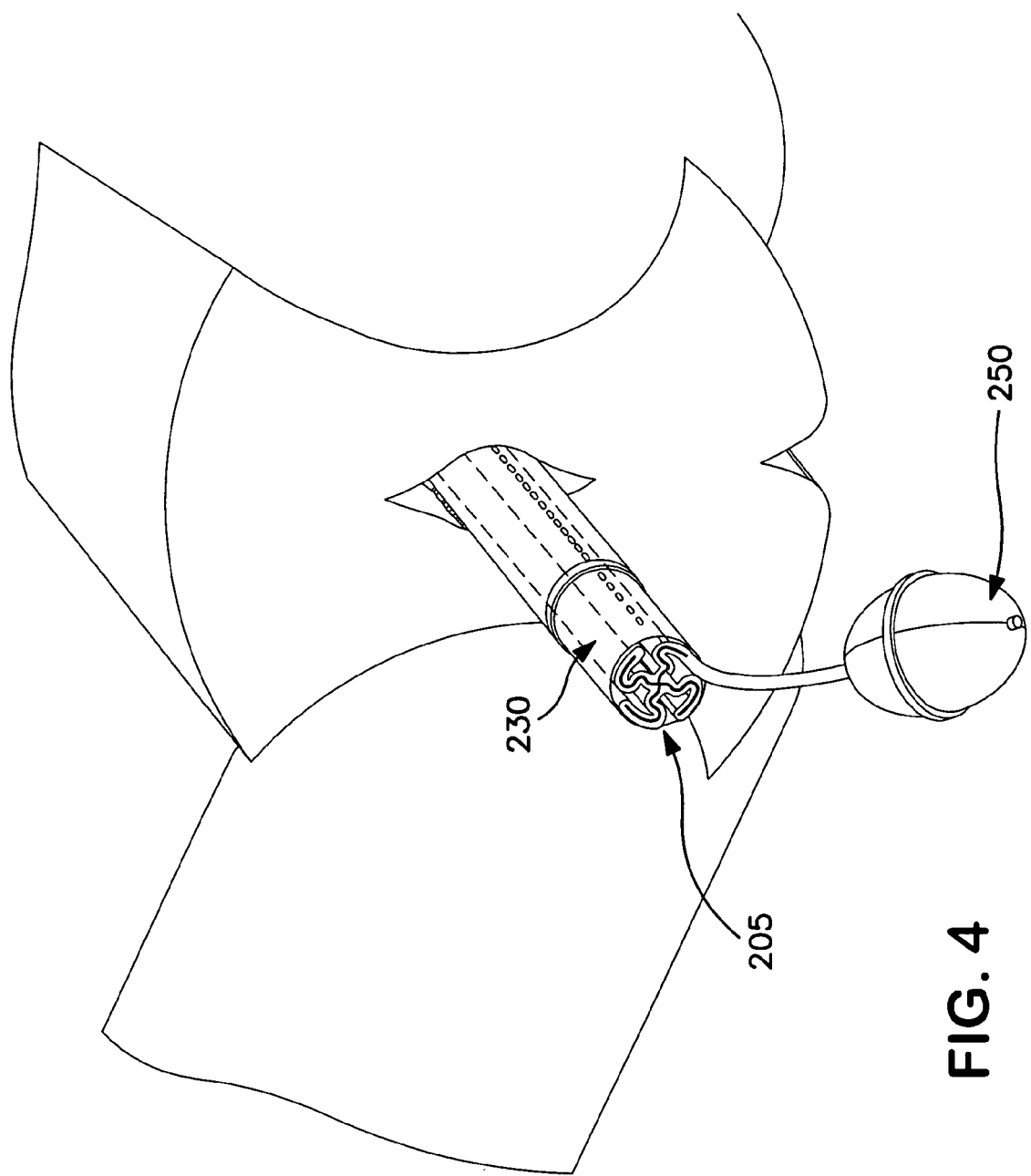
FIG. 4 is a perspective view of the speculum of FIG. 3 inserted inside an orifice, according to an embodiment of the present invention.
Figure 5:
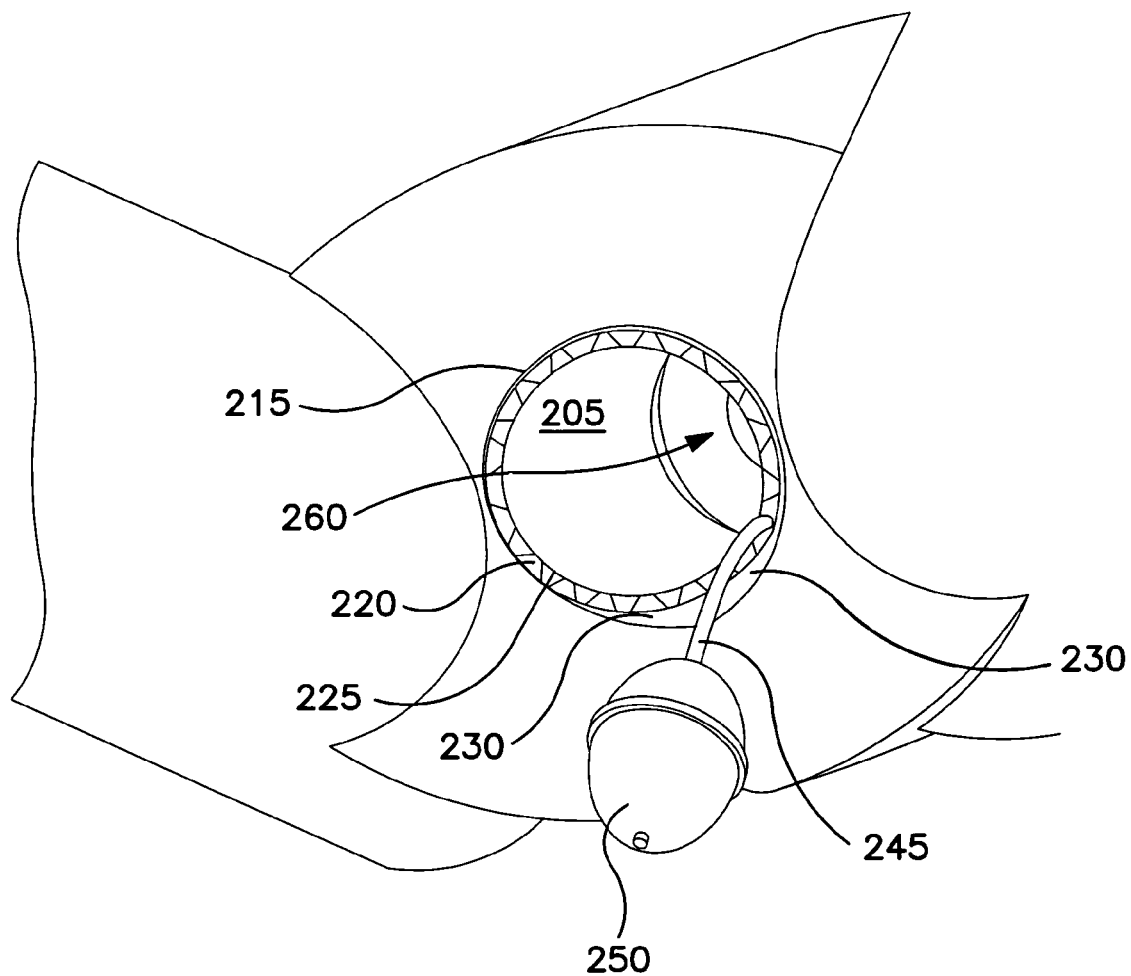
FIG. 5 is a perspective view of the speculum of FIG. 4 inflated inside the orifice with a portion of the applicator remaining attached to the inflation line after inflation, according to an embodiment of the present invention.

Preferred embodiments of the present invention and their advantages may be understood by referring to FIGS. 2–7, like numerals being used for like corresponding parts in the various drawings.

Referring to FIGS. 2–5, an inflatable speculum 200, e.g., an inflatable vaginal speculum, according to an embodiment of the present invention is depicted. Speculum 200 may comprise an inflatable bladder 205, means for inflating bladder 205, and means for deflating bladder 205. For example, the means for inflating bladder 205 may comprise an inflation line 245 connected to bladder 205, and a pump 250 connected to inflation line 245. Specifically, when a user of speculum 200 applies pressure to pump 250, pump 250 may dispense air or a fluid inside bladder 205 via inflation line 245, thereby causing bladder 205 to inflate. The means for deflating bladder 205 may comprise a valve 255. Valve 255 may cover an opening (not shown) formed through inflation line 245. When valve is in an open position, air may escape from bladder 205 via the opening in inflation line 245, thereby deflating bladder 205.

In an embodiment of the present invention, bladder 205 may comprise a baffle member 270, and when bladder 205 is inflated, bladder 205 also may comprise a first opening 260 formed between a first end of bladder 205 and a second end of bladder 205. Baffle member 270 may comprise a first flexible layer 215, a second flexible layer 225, and a plurality of baffles 220, e.g., a plurality of flexible, plastic baffles, positioned between and attached to each of first flexible layer 215 and second flexible layer 225. For example, first flexible layer 215 and second flexible layer 225 may be a single sheet of flexible plastic folded over itself and then sealed, such that the sheet of flexible plastic encloses baffles 220. Moreover, inflation line 245 may be positioned within one of baffles 245, such that when the user applies pressure to pump 250, air or fluid enters baffles 220, thereby causing baffles 220, first flexible layer 215, and second flexible layer 225 to inflate. For example, inflated baffles 220 may have a substantially trapezoidal cross-sectional shape. The trapezoidal shaped baffles may withstand more pressure than triangle shaped baffles before collapsing. Speculum 200 also may comprise at least one light source (not shown) positioned within at least one of baffles 220. For example, the light source may comprise at least one tubular, chemiluminescent light source positioned within at least one of baffles 220, which may be activated by bending the light source.

Figure 7:
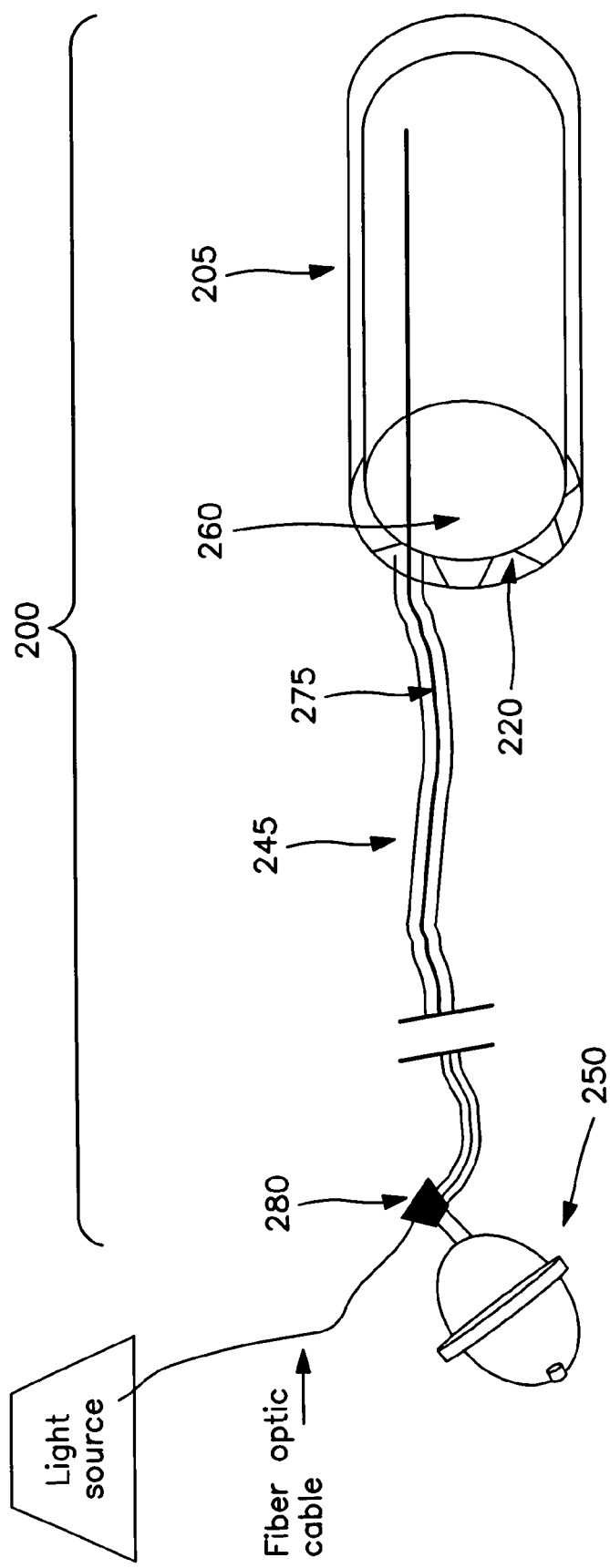
FIG. 7 is a perspective view of a speculum having a light source for illuminating the orifice, according to an embodiment of the present invention.

Alternatively, and referring to FIG. 7, the at least one light source may comprise a beam of light for illuminating the orifice. For example, a reusable lamp, e.g., a 120 Volt/150 Watt halogen light, may provide the beam of light to the orifice via a fiber optic cable. The fiber optic cable may be connected to a manifold 280 which includes a female luer and pump 250. In this embodiment, speculum 200 may comprise a fiber optic element 275. Specifically, a first portion of fiber optic element 275 may be positioned within inflation line 245, and a second portion of fiber optic element 275 may be positioned within one of baffles 220. For example, fiber optic element may have a diameter of about a 1.5 mm (about 0.059 inches), and the second portion of fiber optic element 275 may terminate about 25.4 mm (about 1 inch) from an end of baffle 220. Moreover, inflation line 245 may be connected to pump 250, and pump 250 may be connected to the fiber optic cable, which allows the fiber optic cable to contact fiber optic element 275 for the transmission of light inside the orifice.

In an embodiment of the present invention, bladder 205 may comprise a baffle member 270, and when bladder 205 is inflated, bladder 205 also may comprise a first opening 260 formed between a first end of bladder 205 and a second end of bladder 205. Baffle member 270 may comprise a first flexible layer 215, a second flexible layer 225, and a plurality of baffles 220, e.g., a plurality of flexible, plastic baffles, positioned between and attached to each of first flexible layer 215 and second flexible layer 225. For example, first flexible layer 215 and second flexible layer 225 may be a single sheet of flexible plastic folded over itself and then sealed, such that the sheet of flexible plastic encloses baffles 220. Moreover, inflation line 245 may be positioned within one of baffles 245, such that when the user applies pressure to pump 250, air or fluid enters baffles 220, thereby causing baffles 220, first flexible layer 215, and second flexible layer 225 to inflate. For example, inflated baffles 220 may have a substantially trapezoidal cross-sectional shape. The trapezoidal shaped baffles may withstand more pressure than triangle shaped baffles before collapsing. Referring to a cutaway portion 290 of FIG. 3, speculum 200 also may comprise at least one light source 295 positioned within at least one of baffles 220. For example, the light source may comprise at least one tubular, chemiluminescent light source positioned within at least one of baffles 220, which may be activated by bending the light source.

Figure 6:
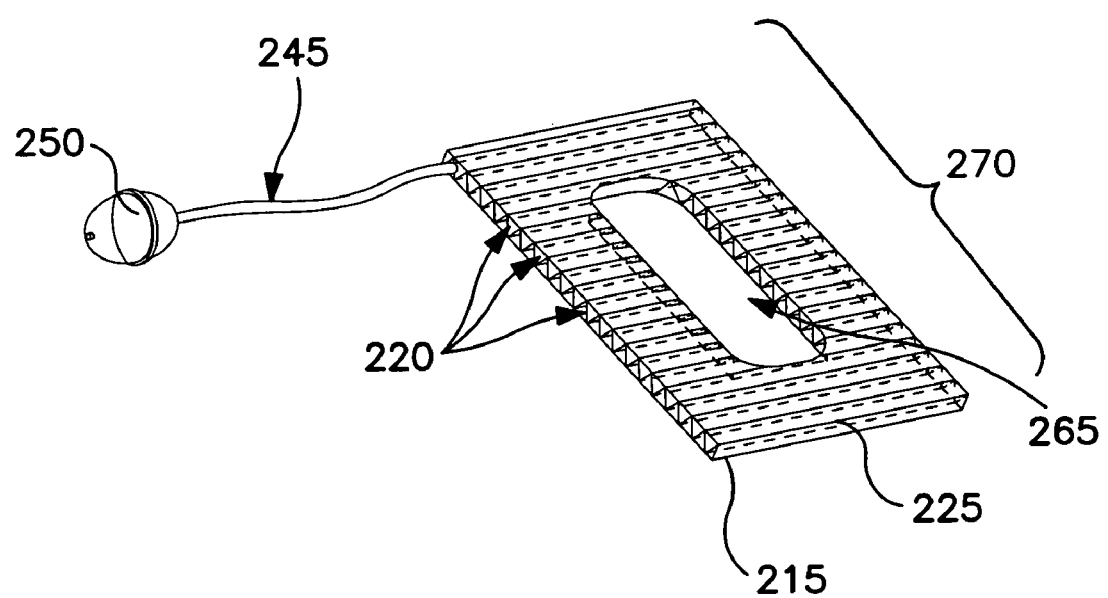
FIG. 6 is a perspective view of a speculum having an opening formed through a wall of an inflatable bladder, according to an embodiment of the present invention.

Referring to FIG. 6, in another embodiment of the present invention, bladder 205 also may comprise a second opening 265 formed through a wall of bladder 205. When bladder 205 is inflated and positioned inside an orifice, second opening 265 allows the user of speculum 200 to obtain a sample from a wall of the orifice without having to remove bladder 205 from the orifice.

In operation, bladder 205 may be inserted inside the orifice, and subsequently may be inflated. For example, the user of speculum 200 may apply a lubricant to an exterior surface of applicator 230. When bladder 205 inflates, applicator 230 may tear along perforations 235 and separate from bladder 205, and bladder 205 may expand to conform to a shape of the orifice. Nevertheless, applicator 230 may remain attached to inflation line 245 via attachment portion 230. Moreover, when bladder 205 is inflated, the lubrication layer contacts the walls of the orifice, and the user of speculum 200 may view an inside of the orifice via first opening 260 or obtain a sample of a wall of the orifice via second opening 265, or both. The user also may activate the light source to more readily view the inside of the orifice or to obtain the sample of the orifice, or both. When the user of speculum 200 is finished, the user may deflate bladder 205 by moving valve 255 from an off position to an on position, thereby exposing the opening formed though inflation line 245. The user then may remove bladder 205 and applicator 230, e.g., by pulling inflation line 245 in a direction away from the orifice, and dispose of speculum 200.

While the invention has been described in connection with preferred embodiments, it will be understood by those of ordinary skill in the art that other variations and modifications of the preferred embodiments described above may be made without departing from the scope of the invention. Other embodiments will be apparent to those of ordinary skill in the art from a consideration of the specification or practice of the invention disclosed herein. It is intended that the specification and the described examples are considered as exemplary only, with the true scope and spirit of the invention indicated by the following claims.

What is claimed is:

1. An inflatable speculum adapted to be positioned within an orifice, comprising:
    an inflatable bladder, wherein when the inflatable bladder is inflated, the inflatable bladder comprises:
        a baffle member comprising a plurality of baffles, wherein each of the plurality of baffles has a substantially trapezoidal cross-sectional shape;
        a particular opening formed between a first end of the inflatable bladder and a second end of the inflatable bladder for viewing an inside of the orifice;
    means for inflating the inflatable bladder, wherein the means for inflating the inflatable bladder comprises:
        an inflation line attached to the inflatable bladder; and
        a pump attached to the inflation line;
    a light source;
    a manifold;
    a fiber optic cable coupled to the light source and the manifold, wherein the inflation line is coupled to the manifold; and
    at least one fiber optic element coupled to the fiber optic cable for illuminating the inside of the orifice, wherein a first portion of the fiber optic element is positioned within the inflation line, and a second portion of the fiber optic element is positioned within a corresponding one of the plurality of baffles.

2. The speculum of claim 1, wherein the inflation line is positioned within one of the plurality baffles.

3. The speculum of claim 1, wherein each of the pump and the inflation line are adapted to dispense at least one of air and a fluid into the inflatable bladder.

4. The speculum of claim 1, further comprising means for deflating the inflatable bladder.

5. The speculum of claim 6, wherein the means for deflating the inflatable bladder comprises a valve for releasing air from inside the inflatable bladder.

6. The speculum of claim 1, further comprising at least one light source positioned within one of the plurality of baffles, wherein the at least one light source comprises a tubular, chemiluminescent light source.

7. The speculum of claim 1, wherein the inflatable bladder further comprises at least one further opening formed through the baffle member for allowing access to at least one wall of the orifice.

8. An inflatable speculum adapted to be positioned within an orifice, comprising:
    an inflatable bladder, wherein when the inflatable bladder is inflated, the inflatable bladder comprises:
        a baffle member comprising a plurality of baffles, wherein each of the plurality of baffles has a substantially trapezoidal cross-sectional shape;
        a particular opening formed between a first end of the inflatable bladder and a second end of the inflatable bladder for viewing an inside of the orifice;
    means for inflating the inflatable bladder; and
    an applicator, wherein when the inflatable bladder is not inflated, a first member of the applicator encloses the inflatable bladder and a second member of the applicator is attached to the means for inflating, and when the inflatable bladder is inflated, a particular portion of the first member is torn and the second member remains attached to the means for inflating.

9. The speculum of claim 8, wherein the particular portion of the first member is perforated.

10. The speculum of claim 8, further comprising a lubrication layer positioned between at least a portion of an interior surface the applicator and an exterior surface of the inflatable bladder, such that when the particular portion of the first member is torn, the lubrication layer is in contact with a wall of the orifice.

11. The speculum of claim 8, wherein the baffle member further comprises:
    a first flexible layer; and
    a second flexible layer, wherein the plurality of baffles are positioned between the first flexible layer and the second flexible layer, and the plurality of baffles are enclosed by the first flexible layer and the second flexible layer.

12. The speculum of claim 11, wherein each of the first flexible layer, the second flexible layer, and the plurality of baffles comprise a flexible, transparent plastic.

13. An inflatable speculum adapted to be positioned within an orifice, comprising:
    an inflatable bladder, wherein when the inflatable bladder is inflated, the inflatable bladder comprises:
        a first opening formed between a first end of the inflatable bladder and a second end of the inflatable bladder for viewing an inside of the orifice; and
        at least one second opening formed through a wall of the inflatable bladder for allowing access to at least one wall of the orifice,
    means for inflating the inflatable bladder; and
    an applicator, wherein when the inflatable bladder is not inflated, a first member of the applicator encloses the inflatable bladder and a second member of the applicator is attached to the means for inflating, and when the inflatable bladder is inflated, a particular portion of the first member is torn and the second member remains attached to the means for inflating.

14. The speculum of claim 13, wherein the inflatable bladder further comprises a baffle member.

15. The speculum of claim 14, wherein the baffle member comprises:
    a first flexible layer;
    a second flexible layer; and
    a plurality of baffles positioned between the first flexible layer and the second flexible layer, wherein the plurality of baffles are enclosed by the first flexible layer and the second flexible layer.

16. The speculum of claim 15, wherein each of the plurality of baffles has a substantially trapezoidal cross-sectional shape.

17. The speculum of claim 15, wherein the wall of the inflatable bladder comprises the baffle member, and the at least one second opening is formed through the baffle member.

18. The speculum of claim 15, further comprising means for inflating the inflatable bladder.

19. The speculum of claim 18, wherein the means for inflating the inflatable bladder comprises:
    an inflation line attached to the inflatable bladder; and
    a pump attached to the inflation line.

20. The speculum of claim 19, wherein the inflation line is positioned within one of the plurality baffles.

21. The speculum of claim 19, wherein each of the pump and the inflation line are adapted to dispense at least one of air and a fluid into the inflatable bladder.

22. The speculum of claim 19, further comprising means for deflating the inflatable bladder.

23. The speculum of claim 22, wherein the means for deflating the inflatable bladder comprises a valve for releasing air from inside the inflatable bladder.

24. The speculum of claim 15, further comprising at least one light source positioned within one of the plurality of baffles.

25. The speculum of claim 24, wherein the at least one light source comprises a tubular, chemiluminescent light source.

26. The speculum of claim 13, wherein the particular portion of the first member is perforated.

27. The speculum of claim 13, further comprising a lubrication layer positioned between at least a portion of an interior surface the applicator and an exterior surface of the inflatable bladder, such that when the particular portion of the first member is torn, the lubrication layer is in contact with a wall of the orifice.

28. An inflatable speculum adapted to be positioned within an orifice, comprising:
  an inflatable bladder, wherein when the inflatable bladder is inflated, the inflatable bladder comprises:
    an opening formed between a first end of the inflatable bladder and a second end of the inflatable bladder;
  means for inflating the inflatable bladder; and
  an applicator, wherein when the inflatable bladder is not inflated, a first member of the applicator encloses the inflatable bladder and a second member of the applicator is attached to the means for inflating, and when the inflatable bladder is inflated, a particular portion of the first member is torn and the second member remains attached to the means for inflating.

29. The speculum of claim 28, wherein the means for inflating the inflatable bladder comprises:
  an inflation line attached to the inflatable bladder; and
  a pump attached to the inflation line, wherein the second member of the applicator is attached to at least one portion of the inflation line.

30. The speculum of claim 28, further comprising a lubrication layer positioned between at least a portion of an interior surface the applicator and an exterior surface of the inflatable bladder, such that when the particular portion of the first member is torn, the lubrication layer is in contact with a wall of the orifice.

31. The speculum of claim 28, wherein the inflatable bladder further comprises a baffle member.

32. The speculum of claim 31, wherein the baffle member comprises:
  a first flexible layer;
  a second flexible layer; and
  a plurality of baffles positioned between the first flexible layer and the second flexible layer, wherein the plurality of baffles are enclosed by the first flexible layer and the second flexible layer.

33. The speculum of claim 32, wherein each of the plurality of baffles has a substantially trapezoidal cross-sectional shape.

* * * * *